US00PP32180P3

(12) United States Plant Patent
Sproul

(10) Patent No.: US PP32,180 P3
(45) Date of Patent: Sep. 15, 2020

(54) FLORIBUNDA ROSE PLANT NAMED 'SPROFLORED'

(50) Latin Name: *Rosa hybrida*
Varietal Denomination: Sproflored

(71) Applicant: The Conard-Pyle Company, West Grove, PA (US)

(72) Inventor: James Sproul, Bakersfield, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,675

(22) Filed: Dec. 19, 2018

(65) Prior Publication Data

US 2020/0205326 P1 Jun. 25, 2020

(51) Int. Cl.
*A01H 5/02* (2018.01)
*A01H 6/74* (2018.01)

(52) U.S. Cl.
USPC ..... Plt./151
CPC ..... *A01H 6/749* (2018.05)

(58) Field of Classification Search
USPC ..... Plt./151, 150, 140, 108
CPC ..... A01H 5/0222; A01H 5/02; A01H 5/00; A01H 6/749; A01H 6/74
See application file for complete search history.

(56) References Cited

U.S. PATENT DOCUMENTS

PP15,878 P3 7/2005 Meilland
PP23,549 P3 4/2013 Sproul

OTHER PUBLICATIONS

DocBox Saunders Brothers, Inc. Jun. 14, 2018 [online] retrieved on Nov. 26, 2019, retrieved from the Internet at https://homedocbox.com/Landscaping/108195306-Saunders-brothers-inc.html, pp. 1,15. (Year: 2018).*

Overdevest Nurseries L.P. Catalog 2019 [online] retrieved on Nov. 26, 2019, retrieved from the Internet at https://www.grownbyoverdevest.com/wp-content/uploads/2019/02/2019-Overdevest-Catalog.pdf, cover page and p. 41. (Year: 2019).*

* cited by examiner

*Primary Examiner* — June Hwu
(74) *Attorney, Agent, or Firm* — Panitch Schwarze Belisario & Nadel LLP

(57) ABSTRACT

A new and distinct variety of floribunda rose plant, herein referred to by its cultivar name, 'Sproflored', is provided which forms abundantly on a substantially continuous basis attractive, cup shaped deep red blossoms. Attractive, glossy, dark green foliage is formed, which contrasts beautifully with the blossoms. The vegetation is vigorous and the growth habit is very bushy and rounded. The new variety is well suited for providing attractive ornamentation in the landscape.

1 Drawing Sheet

Botanical/commercial classification:
Latin name—*Rosa hybrida.*
Common name—Floribunda Rose Plant.
Varietal denomination: 'Sproflored'.

SUMMARY OF THE INVENTION

The new variety of *Rosa hybrida* floribunda rose plant was created during April of 2008 in Bakersfield, Calif., U.S.A., by artificial pollination wherein two parents were crossed which previously had been studied in the hope that they would contribute the desired characteristics. The female parent (i.e., the seed parent) was an unnamed seedling (non-patented). The male parent (i.e., the pollen parent) was the 'Sprothrive' variety (U.S. Plant Pat. No. 23,549).

The parentage of the new variety can be summarized as follows:

unnamed seedling x 'Sprothrive'

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms attractive, cup shaped, deep red colored blossoms abundantly and substantially continuously,
(b) displays a very bushy and rounded growth habit,
(c) forms vigorous vegetation,
(d) provides attractive ornamental glossy, dark green foliage, and
(e) exhibits good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seedling female parent (i.e., the seed parent) displays peach colored blossoms, whereas the new variety displays deep red colored blossoms and the 'Sprothrive' variety (i.e., the pollen parent) provides less petals and is less compact in habit compared to the new variety. Moreover, the new variety can be readily distinguished from other similar non-parental varieties. For example, the 'MEIBIO- NEL' variety (U.S. Plant Pat. No. 15,878) displays less petal, provides a larger flower size, and exhibits foliage that is less glossy compared to the new variety.

The new variety has been found to undergo asexual propagation in Wasco, Calif. by a number of routes, including vegetative cuttings from stem. Asexual propagation by stem vegetative cuttings in Wasco, Calif. has shown that the characteristics of the new variety are stable and are strictly transmissible by such asexual propagation from one generation to another. Accordingly, the new variety undergoes asexual propagation in a true-to-type manner.

The new variety has been named 'Sproflored'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was observed during July 2016 while growing on its own roots and growing outdoors at Watsonville, Calif., U.S.A.

FIG. 1—illustrates a specimen of a plant with blooms at varying stages of opening and is in a field planted with other roses.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during July while growing on their own roots at Cochranville, Pa., U.S.A.

Class: Floribunda Rose Plant.

Plant:

*Habit*.—Very busy and round.

*Height*.—Approximately 40.0 cm on average from the top of the soil plane.

*Width*.—Approximately 40.0 cm on average.

*Young shoot*.—Medium anthocyanin coloration.

Branches:

*Color*.—Young stems: commonly near Yellow-Green Group 145A. — old wood: commonly near Yellow-Green Group 144A.

*Length*.—Main stems: approximately 34.0 cm on average. — secondary stems: approximately 14.0 cm on average.

*Thorns*.—Young thorns: length is approximately 7.0 mm on average, width is approximately 6.0 mm at point of attachment, and color is commonly between near Greyed-Orange Group 164A and Greyed-Orange Group 164C. — old thorns: length is approximately 6.0 mm on average, width is approximately 4.0 mm on average, and color is commonly near Brown Group N200A.

Foliage:

*General appearance*.—Dark green with a glossy aspect.

*Number of leaflets*.—3, 5, and 7.

5-*leaflet leaf*.—Length: approximately 10.0 cm on average. — width: approximately 7.5 cm on average.

*Young foliage*.—Upper surface color: commonly near Yellow-Green Group 146A. — under surface color: commonly near Yellow-Green Group 146C.

*Old foliage*.—Upper surface color: commonly near Green Group 139A. — under surface color: commonly near Green Group 138A.

*Glossiness of upper surface of the leaf*.—Medium.

Leaflets:

*Shape*.—Ovate.

*Texture*.—Upper and under surface is smooth.

*Terminal leaflet*.—Length: approximately 4.5 cm on average. — width: approximately 3.0 cm on average. — shape: apex is acute and base is rounded.

*Lower leaflet*.—Length: approximately 2.5 cm on average. — width: approximately 2.0 cm on average.

*Leaflet margin*.—Serrate; undulation is very weak.

*Petiole*.—Upper surface: color is commonly near Green Group 138A and texture is smooth. — under surface: color is commonly near Green Group 138B and texture is glandular with some small prickles.

*Rachis*.—Color of upper surface: commonly near Green Group 138A. — color of under surface: cam only near Green Group 138B. — texture: upper surface is smooth and under surface is mostly smooth with a few small prickles.

*Stipules*.—Margin: entire to erose. — length: approximately 1.8 cm on average. — width: approximately 9.0 mm on average. — color of upper surface: commonly near Green Group 137A. — color of under surface: commonly near Green Group 137B.

Inflorescence:

*Number of flowers*.—Generally about 24 blooms on average on a plant at once.

*Number of blooms per stem*.—Generally between 1 to 8 blooms per stem on average.

*Bud*.—Shape: ovoid. — length: approximately 1.2 cm on average. — width: approximately 1.3 cm on average. — color when opening: commonly near Greyed-Purple Group 186A.

*Sepals*.—Number: commonly 5 on average. — length: approximately 1.6 cm on average. — width: approximately near 9.0 mm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 145A; puberulent.

*Receptacle*.—Undeveloped seeds are found lining the inner wall and bottom portion of the receptacle. — color: commonly near Green Group 141C to near Purple Group N77C at the top. — diameter: approximately 6.0 mm on average. — surface texture: smooth. — shape: round.

*Peduncle*.—Length: approximately 3.5 cm on average. — diameter: approximately 5.0 mm on average. — surface texture: sparely covered in short, flexible thorns that measure less than 2.0 mm in length. — color: commonly near Yellow-Green Group 146B.

*Flower*.—Diameter: approximately 4.5 cm on average. — height: approximately 3.0 cm on average. — duration: flower is on the plant approximately 18 days. — shape: cup shaped. — form:

double. — number of petals under normal conditions: approximately 31 petals on average. — shape of the petal: overall: broadly obovate. base: cuneate. apex: slightly cuspidate. — petal length: approximately 2.0 cm on average. — petal width: approximately 2.4 cm on average. — petal margin: entire. — petal incision: none. — petal undulation: weak. — reflexing of the petal margin: weak. — petal drop: good. — fragrance: none noticeable. — petal color when opening begins and of mature petal: upper surface: at the point of attachment commonly near Yellow Group 13A; working toward the apex transitions to near Red Group 53A. under surface: at the point of attachment commonly near Yellow Group 13B; working toward the apex transitions to near Red Group 53C. — petal color at end of blooming: upper surface: at the point of attachment commonly near Yellow Group 8A blending to near Red-Purple Group N66A. under surface: at the point of attachment commonly near Yellow Group 8C blending to near Red-Purple Group N66C. basal spot on the upper surface of the petal: small.

*Stamen*.—Number is approximately 85 on average. — anthers: number is approximately 85 on average and coloration is commonly near Yellow-Orange Group 23C. — filaments: length is approximately 1.0 cm on average and coloration is commonly near Yellow-Orange Group 21C.

*Pistils*.—Arrangement is separate and free; number is approximately 38 on average. — styles: length is approximately 5.0 mm on average and coloration at the base is commonly near Yellow-Green Group 150D and transitions to near Orange-Red Group N34C at the apex. — stigmas: diameter is approximately 1.0 mm on average and coloration is commonly near Yellow Group 6C.

*Pollen*.—Color is commonly near Yellow-Orange Group 23B and a moderate amount is present.

*Hips*.—Shape is round, length is approximately 1.5 cm on average, diameter is approximately 1.5 cm on average, texture is smooth, and coloration is commonly near Yellow-Green Group 146B.

Development:

*Vegetation*.—Vigorous and strong.

*Blooming*.—Abundant and substantially continuous from spring through frost.

*Hardiness zone*.—Zone 5.

*Resistance to disease*.—Good resistance to *Sphaerotheca pannosa*.

*Tolerance or susceptibility to insects*.—None observed to date.

The new 'Sproflored' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda Rose plant characterized by the following combination of characteristics:

(a) forms attractive, cup shaped, deep red colored blossoms abundantly and substantially continuously, (b) displays a very bushy and rounded growth habit, (c) forms vigorous vegetation, (d) provides attractive ornamental glossy, dark green foliage, and (e) exhibits good disease resistance;

substantially as herein shown and described.

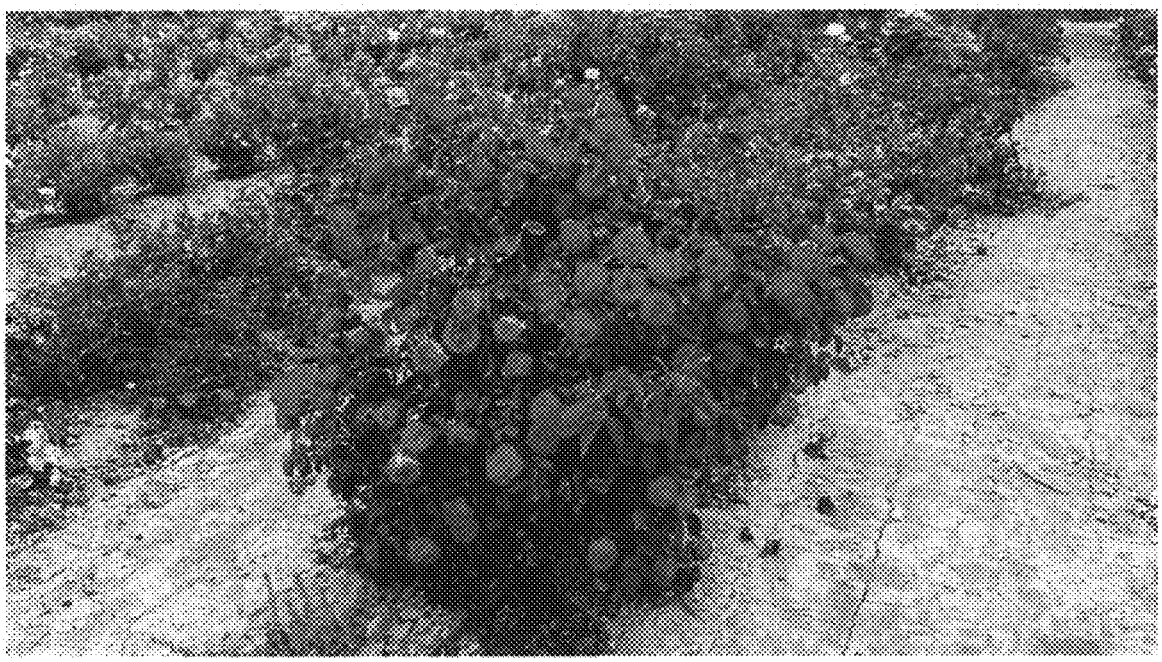

* * * * *